United States Patent [19]

St. George et al.

[11] Patent Number: 4,724,267
[45] Date of Patent: Feb. 9, 1988

[54] NEW HALOACYL AROMATIC MONOMERS VIA A COUPLING REACTION

[75] Inventors: George M. St. George; Marlin E. Walters, both of Lake Jackson, Tex.

[73] Assignee: The Dow Chemical Company, Midland, Mich.

[21] Appl. No.: 866,853

[22] Filed: May 23, 1986

Related U.S. Application Data

[63] Continuation-in-part of Ser. No. 692,461, Jan. 18, 1985, abandoned.

[51] Int. Cl.$^4$ ............................................. C07C 151/00
[52] U.S. Cl. ........................................ 568/20; 568/13; 568/16; 568/43; 568/28; 568/29; 568/30; 568/31; 568/36; 568/37; 568/328; 568/331; 568/332; 564/428; 564/429; 564/430; 564/431; 564/433
[58] Field of Search ............... 568/328, 331, 43, 332, 568/32, 33, 37, 13, 16, 43, 28, 29, 30, 31, 36; 564/428, 429, 430, 431, 433

[56] References Cited

U.S. PATENT DOCUMENTS

| | | | |
|---|---|---|---|
| 2,766,298 | 10/1956 | Guthrie et al. | 570/192 |
| 2,788,374 | 9/1957 | Stair | 570/192 |
| 3,150,187 | 9/1964 | Cavallini et al. | 568/331 |
| 3,285,997 | 11/1968 | Rubens | 568/331 |
| 3,450,772 | 6/1969 | Bridges et al. | 568/331 |
| 3,734,884 | 5/1973 | Daims et al. | 528/220 |
| 3,736,293 | 5/1973 | Novak | 528/226 |
| 3,809,682 | 5/1974 | Studinka et al. | 528/220 |
| 3,840,580 | 10/1974 | Feasey et al. | 568/331 |
| 3,932,527 | 1/1976 | Metcalf et al. | 570/192 |
| 4,396,755 | 8/1983 | Rose | 528/220 |

*Primary Examiner*—James H. Reamer
*Attorney, Agent, or Firm*—A. Cooper Ancona

[57] ABSTRACT

Bis(haloacylaromatic) compounds have been made by a new process in which monohaloacylated aromatic compounds have been reacted by a coupling reaction. These bis(haloacylaromatic) compounds can be employed as monomers in the preparation of polyesters and polyamides which have easy processability. The monohaloacylated compound is coupled by reacting two moles of the monomer with a carbon or sulfur compound containing at least two halogen atoms in the presence of a Friedel-Crafts catalyst.

37 Claims, No Drawings

NEW HALOACYL AROMATIC MONOMERS VIA A COUPLING REACTION

CROSS-REFERENCE TO RELATED APPLICATION

This application is a continuation-in-part of copending application Ser. No. 692,461 filed Jan. 18, 1985 now abandoned.

BACKGROUND OF THE INVENTION

Trihaloacyl derivatives of bisphenols and aromatic ethers, e.g. 4,4'isopropylidene diphenol and diphenyl ether, have been disclosed in copending patent applications of one of the present inventors NEW HALOACYL DERIVATIVES OF BISPHENOLS (Ser. No. 647,282, filed Sept. 4, 1984) and HALOACETYL DERIVATIVES OF AROMATIC COMPOUNDS (Ser. No. 858,133, filed Apr. 30, 1986). Such monomers have been found to be useful in preparing polyesters and polyamides. The formation of the haloacetyl derivatives of aromatic compounds, however, suffers from the drawback of the large amounts of Friedel-Crafts catalyst required. Since the monoacylated diphenyl ether can be made conveniently with substoichiometric quantities of Friedel-Crafts catalyst, it would be advantageous to make bisacylated materials by coupling the monoacylated material. Even if a stoichiometric quantity of a Friedel-Crafts catalyst is used in the coupling reaction, the net amount of catalyst per bisacylated product would be roughly half that required in the one-step bisacylation. The bisacylated monomers made according to the present process are useful in modifying the properties of polymers made from them.

The present invention is to a process to obtain such monomers and products made thereby.

SUMMARY OF THE INVENTION

Bis(haloacylaromatic) compounds have been made by a new process in which monohaloacylated aromatic compounds have been reacted by a coupling reaction. These bis(haloacylaromatic) compounds can be employed as monomers in the preparation of polyesters and polyamides which have easy processability. The monohaloacylated compound is coupled by reaction two moles of the monomer with a carbon or sulfur compound containing at least two halogen atoms in the presence of a Friedel-Crafts catalyst.

DETAILED DESCRIPTION OF THE INVENTION

A coupling reaction is employed to produce trihaloacyl derivatives of aromatic compounds wherein there are two or more aromatic rings between the two chlorine-containing functional groups. Thus, two moles of a compound having the structure

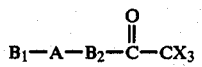

wherein $B_1$ and $B_2$ are independently selected from

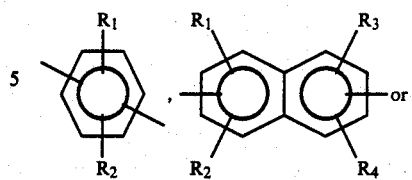

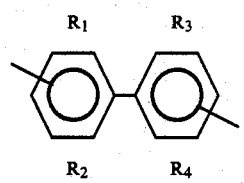

and which may be the same or different and wherein $R_1$, $R_2$, $R_3$ and $R_4$ are independently selected from the group consisting of hydrogen, chlorine, bromine, an alkyl or an alkoxy group having from 1 to 4 carbon atoms, a phenyl group or a substituted phenyl group

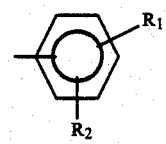

wherein $R_1$ and $R_2$ have the aforesaid meaning, X is chlorine or bromine and A is a single valence bond, oxygen, sulfur,

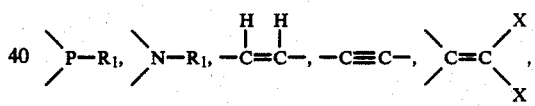

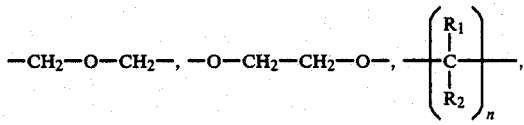

an aromatic group having the formula

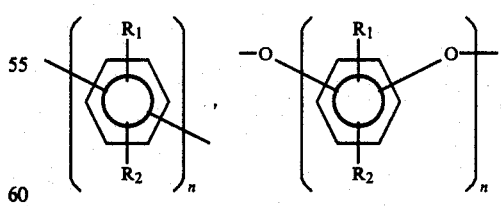

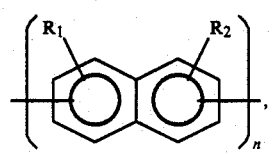

-continued

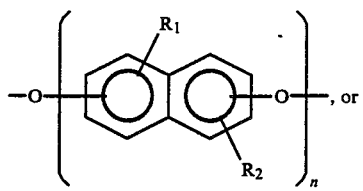

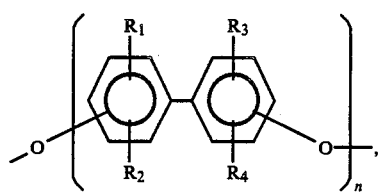

X, $R_1$, $R_2$, $R_3$ and $R_4$ having the aforesaid meanings and wherein n is an integer from 1 to 6, and wherein $B_1$ has one less valence bond than $B_2$; are reacted with a compound having the structure $QX_2$ wherein X has the aforesaid meaning, Q is a

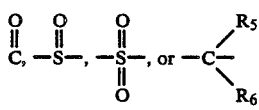

group and wherein $R_5$ and $R_6$ are independently selected from hydrogen, halogen, an alkyl or haloalkyl group having from 1 to 6 carbon atoms or an aryl group having from 6 to 10 carbon atoms.

The product formed has the following formula

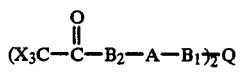

wherein A, $B_1$, $B_2$, X and Q have the aforesaid meanings.

Where both $R_5$ and $R_6$ are halogens they may be hydrolyzed to form the carbonyl group, thus yielding the product having the following formula

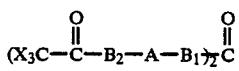

wherein A, $B_1$, $B_2$ and X have the aforesaid meanings.

The catalyst for the coupling reaction is any Lewis acid-type compound which will catalyze the Friedel-Crafts reaction. Compounds useful are, for example, $AlCl_3$, $ZrCl_4$, $TiCl_4$, $TiCl_3$, $TaF_5$, and $HfCl_4$.

The coupling reaction is conducted at temperatures in the range of from about 20 to about 150° C. and preferably from about 50 to about 80° C.

Representative halogen compounds useful as coupling agents are carbon tetrachloride or tetrabromide, methylene chloride 1,1-dichloroethane, phosgene, dibromocarbonyl, tetrachloroethanes, tetrabromoethanes, 1,1-dichloropropane, 2,2-dichloropropane, thionyl chloride, sulfuryl chloride and the like.

It is to be understood that in order for the coupling reaction to proceed at least two halogens must be present in the molecule. The preferred compounds are those which have at least two halogen atoms attached to the same carbon or sulfur atom.

Chlorinated hydrocarbons are useful both as reactants in the coupling reaction and as solvents for the reaction product, provided there is no adverse reaction with the catalyst. Thus, carbon tetrachloride can be used as a reactant and solvent.

The following experiments are representative of the process and products of the present invention. Preparation of a singly trichloroacetylated diphenyl ether is shown together with its use to make its dimeric products.

EXAMPLE 1

Preparation of the Mono-Acetylated Diphenyl Ether

In a typical synthesis of 4-trichloroacetyl phenyl ether, a 500 ml round-bottom flask fitted with a condenser, thermometer, and pressure-equalizing dropping funnel was charged with 200 ml trichloroacetyl chloride (TCAC, 1.8 moles) and 15 g $AlCl_3$ (0.11 moles). The funnel was charged with 80 ml phenyl ether (0.50 moles). The system was purged with nitrogen, and the phenyl ether was added slowly to the $AlCl_3$/TCAC slurry at room temperature with stirring. The temperature was then raised to 85° C. After 2 hours, gas chromatography showed only the monosubstituted phenyl ether, with no phenyl ether remaining and little or no 4,4'-bis-(trichloroacetyl)phenyl ether. The resulting mixture was quenched in ice/HCl.

As the mixture approached room temperature, the rate of the hydrolysis of the excess TCAC became more rapid and its exothermic nature raised the temperature more rapidly. Sufficient time was allowed for completion of hydrolysis and for the reaction mixture to return to room temperature.

The product was extracted with $CH_2Cl_2$. The organic phase was washed with water, dried with $Na_2SO_4$, and stripped on a rotary evaporator. The product was removed from dark impurities by distillation at 2 torr and 180° C. to yield 110 g of a colorless or pale yellow oil (0.35 moles 70%). The oil solidified on standing to form crystals, m.p. 46°-48° C.

In the following example the coupling of the product of Example 1 is shown.

EXAMPLE 2

Coupling the Acylaromatic Compound

In a 500 ml round-bottom flask were combined 31 g 4-(trichloroacetyl)phenyl ether (0.098 mole); 200 ml $CCl_4$; and 13 g $AlCl_3$ (0.098 mole). A condenser was fitted to the flask, and the mixture was heated with vigorous stirring at 60° C. for 3 hours. During this time, a dark red, viscous gum separated from the $CCl_4$. This was taken up into the minimum amount of $CH_2Cl_2$ (ca. 200 ml) and the $AlCl_3$ was quenched by pouring the $CH_2Cl_2$ solution over 300 g ice and stirring vigorously. On standing a few minutes, two phases separated, the organic phase was dried, and the $CH_2Cl_2$ was removed, leaving 33.2 g of a dark brown oil (0.047 mole, 94% crude yield). For formation of the ketone derivative (see Example 3) no further purification is necessary. The product, bis-(4-[4'-(trichloroacetyl)phenoxy]-phenyl)dichloromethane has the structure

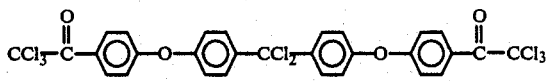

Similar products can be made using 1,1-dichloroethane, 1,1,2-trichloroethane and the like.

EXAMPLE 3

Hydrolyzing the Coupled Adduct

A 250 ml round-bottom flask was charged with the product of Example 2, 29.6 g (0.042 mole); 150 ml THF; and 20 ml 0.1N HCl. (A basic solution will hydrolyze the trichloroacetyl groups.) The flask was fitted with a condenser, and the mixture was stirred at reflux for 2 hours. Upon standing and cooling, two phases separated. The organic phase was dried, and the volatiles were removed to give 28.2 g of a tan-colored gum. Precipitation from acetone and alcohol gave 21.6 g of a white powder (0.033 moles, 79%), m.p. 125° C. (uncorrected). The product, bis-(4-[4'-(trichloroacetyl)-phenoxy]phenyl)methanone, has the structure

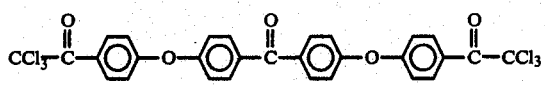

Acetone, dimethyl sulfoxide or dimethyl formamide also can be used as the solvent in the above hydrolysis reaction.

The above compound can also be made directly by reacting the singly-haloacylated compound with phosgene or dibromocarbonyl. Other coupling reactions can be accomplished with the analogous sulfur compound to form sulfoxide-compounds. Illustrations of the use of sulfur compound are shown in Examples 4 and 5 following.

EXAMPLE 4

Coupling with Thionyl Chloride

A 500-ml, three-neck flask, fitted with a thermometer, a condenser, a pressure-equalizing dropping funnel, a nitrogen inlet, a gas outlet and containing a stirring bar was charged with 200 ml 1,2-dichloroethane; 4-(trichloroacetyl)phenyl ether (TAPE, 31 g, 98 mmole); and AlCl3 (20 g, 150 mmol). A solution of SOCl2 (7 ml, 96 mmole) in 1,2-dichloroethane (33 ml) was added dropwise via the dropping funnel to the rapidly stirred mixture under nitrogen. The mixture was heated at 65° C. for 2.5 hours, at which time, no remaining TAPE was observed by gas chromatography. The mixture was quenched in ice/HCl. The heavier, organic layer was separated, washed twice with water, and dried with MgSO4. The volatiles were removed by rotary evaporation to give a yellow oil (39 g). Chromatography on a large (9×72 cm) Kieselguhr "dry" column developed with 1:3 ethyl acetate:hexane gave bis(4-[4-(trichloroacetyl)phenoxy]phenyl)sulfoxide, 13.7 g, 20 mmol, 41%). Evaporation of a 3:1 hexane:CH2Cl2 solution gave long, pale-yellow needles, m.p. 154.5°-156° C. which has the structure

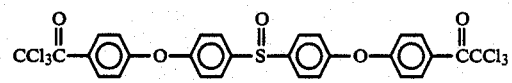

as shown by nmr and IR analyses.

Sulfuryl chloride (SO2Cl2) can also be used to couple the mono(trihaloacyl) aromatic compounds as shown by the following example.

EXAMPLE 5

Coupling with Sulfuryl Chloride

The apparatus was the same as that used in Example 4. The flask was charged with 1,2-dichloroethane (150 ml); 4-(trichloroacetyl)phenyl ether(TAPE), (31 g, 98 mmole); and AlCl3 (40 g, 300 mmole). SO2Cl2 (25 ml, 310 mmole) was added via the dropping funnel. The mixture was heated at 70° C. until all of the TAPE was consumed (2 hours). Quenching, washing, and drying were performed as per Example 4. Separation by elution through a Kieselguhr column with increasingly polar ethyl acetate-hexane mixtures gave 1-chloro-4-[4-(trichloroacetyl)phenoxy]benzene as a major product, with a smaller amount of bis(4-[4-(trichloroacetyl)-phenoxy]phenyl)sulfone, 2.7 g, 4 mmole, 8%) as a light-green oil, which has the structure

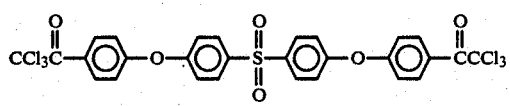

as shown by nmr and IR analyses.

We claim:

1. Bis(haloacylaromatic) compounds having the formula

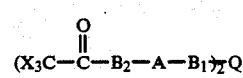

wherein $B_1$ and $B_2$ are independently selected from

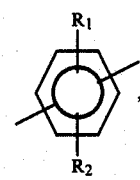 , 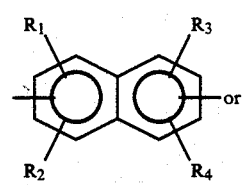 or

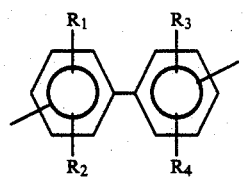

and which may be the same or different and wherein $R_1$, $R_2$, $R_3$ and $R_4$ are independently selected from the group consisting of hydrogen, chlorine, bromine, an alkyl or an alkoxy group having from 1 to 4 carbon atoms, a phenyl group or substituted phenyl group

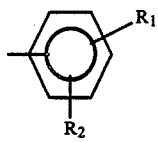

wherein R₁ and R₂ have the aforesaid meaning, X is chlorine or bromine and A is a single valence bond, oxygen, sulfur,

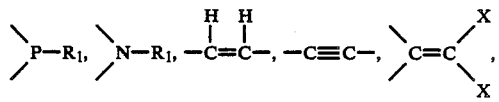

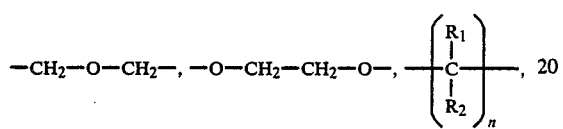

an aromatic group having the formula

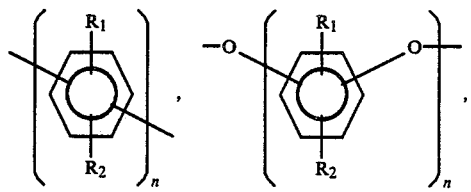

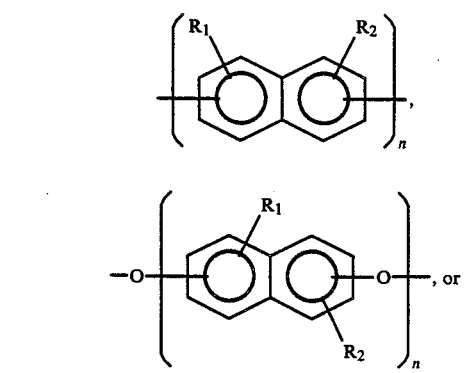

X, R₁, R₂, R₃ and R₄ having the aforesaid meanings and wherein n is an integer from 1 to 6, Q is a

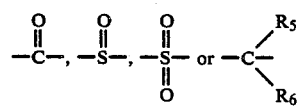

and R₅ and R₆ are independently selected from hydrogen, halogen, an alkyl or haloalkyl group having from 1 to 6 carbon atoms or an aryl group having from 6 to 10 carbon atoms.

2. The compounds of claim 1 wherein A is oxygen.

3. The compounds of claim 1 wherein A is a single valence bond.

4. The compounds of claim 1 wherein A is sulfur.

5. The compounds of claim 1 wherein A is the

radical.

6. The compounds of claim 1 wherein A is the —C≡C— radical.

7. The compounds of claim 1 wherein A is the >N—R₁ radical.

8. The compounds of claim 1 wherein A is >P—R₁.

9. The compounds of claim 1 wherein A is a methylene group.

10. The compounds of claim 2 wherein B₁ and B₂ are each

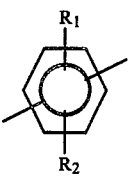

11. The compounds of claim 10 wherein R₁ and R₂ are each hydrogen on each of B₁ and B₂.

12. The compounds of claim 10 wherein at least one of the R groups is an alkyl radical and the remainder are hydrogen.

13. The compounds of claim 12 wherein the alkyl radical is methyl.

14. The compounds of claim 13 wherein B₁ is phenylene and B₂ is tolylene.

15. The compounds of claim 2 wherein B₁ is

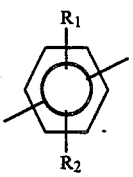

and B₂ is

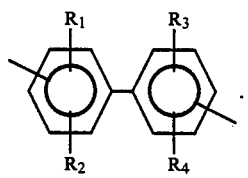

16. The compounds of claim 15 wherein R₁, R₂, R₃ and R₄ are each hydrogen.

17. The compounds of claim 10 wherein A is

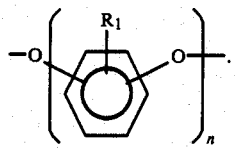

18. The compounds of claim 17 wherein n is 1.
19. The compounds of claim 3 wherein $B_1$ and $B_2$ are each

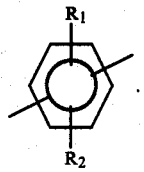

20. The compounds of claim 19 wherein each of $R_1$ and $R_2$ in each of $B_1$ and $B_2$ are hydrogen.
21. The compounds of claim 2 wherein Q is $>CCl_2$.
22. The compounds of claim 3 wherein Q is $>CCl_2$.
23. The compounds of claim 9 wherein Q is $>CCl_2$.
24. The compounds of claim 10 wherein Q is $>CCl_2$.
25. The compounds of claim 20 wherein Q is $>CCl_2$.
26. The compounds of claim 20 wherein Q is $>C=O$.
27. The compounds of claim 2 wherein Q is

28. The compounds of claim 2 where Q is

29. The compounds of claim 10 wherein Q is $>CCl_2$.
30. The compounds of claim 11 wherein Q is $>CCl_2$.
31. The compounds of claim 12 wherein Q is $>CCl_2$.
32. The compounds of claim 13 wherein Q is $>CCl_2$.
33. The compounds of claim 14 wherein Q is $>CCl_2$.
34. The compounds of claim 15 wherein Q is $>CCl_2$.
35. The compounds of claim 16 wherein Q is $>CCl_2$.
36. The compounds of claim 17 wherein Q is $>CCl_2$.
37. The compounds of claim 18 wherein Q is $>CCl_2$.

* * * * *